(12) United States Patent
Zhou et al.

(10) Patent No.: US 10,850,115 B2
(45) Date of Patent: Dec. 1, 2020

(54) SYSTEMS AND METHODS FOR MEDICAL TREATMENT USING A SERIES OF PULSED LASERS

(71) Applicant: GAUSS LASERS TECH (SHANGHAI) CO., LTD., Shanghai (CN)

(72) Inventors: Shiyun Zhou, Shanghai (CN); Hongyan Ren, Shanghai (CN); Ming Wu, Shanghai (CN); Xueyuan Hu, Shanghai (CN); Hang Ni, Shanghai (CN); Tongxin Li, Shanghai (CN); Tuanjie Zhang, Shanghai (CN); Shian Zhou, Shanghai (CN)

(73) Assignee: GAUSS LASERS TECH (SHANGHAI) CO., LTD., Shanghai (CN)

( * ) Notice: Subject to any disclaimer, the term of this patent is extended or adjusted under 35 U.S.C. 154(b) by 194 days.

(21) Appl. No.: 16/171,307

(22) Filed: Oct. 25, 2018

(65) Prior Publication Data
US 2020/0086136 A1 Mar. 19, 2020

Related U.S. Application Data

(63) Continuation of application No. PCT/CN2018/106136, filed on Sep. 18, 2018.

(51) Int. Cl.
*A61N 5/06* (2006.01)
*A61B 18/20* (2006.01)
(Continued)

(52) U.S. Cl.
CPC .......... *A61N 5/0616* (2013.01); *A61B 18/203* (2013.01); *A61B 2017/00061* (2013.01);
(Continued)

(58) Field of Classification Search
CPC ............ A61N 5/0616; A61N 2005/067; A61B 2018/20355; A61B 2018/208;
(Continued)

(56) References Cited

U.S. PATENT DOCUMENTS 9,277,964 B1  3/2016  Hasling
9,550,069 B1  1/2017  Elezzabi
(Continued)

FOREIGN PATENT DOCUMENTS

CN  107007250 A  8/2017

OTHER PUBLICATIONS

International Search Report issued in corresponding International Application No. PCT/CN2018/106136, dated Jun. 17, 2019, 5 pages.

*Primary Examiner* — Catherine M Voorhees
(74) *Attorney, Agent, or Firm* — Bayes PLLC (57) ABSTRACT

Embodiments of systems and methods for medical treatment using a series of pulsed lasers are disclosed. In an example, a system for medical treatment includes a laser source, an optical module, and a controller coupled to the optical module. The laser source is configured to generate a series of pulsed lasers. The optical module is configured to provide a series of focused laser spots on a patient based on the series of pulsed lasers. The controller is configured to control the at least one of the optical module and a stage for holding the patient to move the series of focused laser spots on the patient to form a scan pattern.

30 Claims, 7 Drawing Sheets

(51) Int. Cl.
*A61B 17/00* (2006.01)
*A61N 5/067* (2006.01)
*A61B 18/00* (2006.01)

(52) U.S. Cl.
CPC .............. *A61B 2017/00172* (2013.01); *A61B 2017/00725* (2013.01); *A61B 2018/00648* (2013.01); *A61B 2018/00904* (2013.01); *A61B 2018/208* (2013.01); *A61B 2018/20355* (2017.05); *A61N 2005/067* (2013.01)

(58) Field of Classification Search
CPC ........... A61B 2017/00172; A61B 2017/00061; A61B 2018/00648; A61B 2017/00725; A61B 2018/00904; A61B 18/203
See application file for complete search history.

(56) References Cited

U.S. PATENT DOCUMENTS

| | | | |
|---|---|---|---|
| 2011/0040295 A1* | 2/2011 | Pierce | A61L 2/0011 606/11 |
| 2016/0235586 A1* | 8/2016 | Fu | A61B 18/203 |
| 2017/0000647 A1* | 1/2017 | Schuele | A61F 9/00825 |
| 2017/0266042 A1* | 9/2017 | Palanker | A61F 9/008 |
| 2017/0326003 A1* | 11/2017 | Schuele | A61F 9/00825 |
| 2019/0388151 A1* | 12/2019 | Bhawalkar | A61B 18/203 |

* cited by examiner

SYSTEMS AND METHODS FOR MEDICAL TREATMENT USING A SERIES OF PULSED LASERS

CROSS REFERENCE TO RELATED APPLICATION

This application is continuation of International Application No. PCT/CN2018/106136, filed on Sep. 18, 2018, entitled "SYSTEMS AND METHODS FOR MEDICAL TREATMENT USING A SERIES OF PULSED LASERS," which is hereby incorporated by reference in its entirety.

BACKGROUND

Embodiments of the present disclosure relate to systems and methods for medical treatment using lasers.

The coherency, high monochromaticity, and ability to reach high powers are properties which allow lasers to be used for a variety of medical applications: diagnostic, therapeutic, and surgical, including ophthalmic, dental, oncology, cosmetic, and dermatology. The existing solutions include applying a single, high power, large-sized light-spot directly to the target of human body to perform treatments, or simultaneously applying an array of splitting laser beams on the surface of human skin. The high power of each single pulse, however, may damage the surrounding tissues due to thermal effect. On the other hand, the treatment efficiency of the existing solutions is not ideal due to the relatively low laser power density.

SUMMARY

Embodiments of systems and methods for medical treatment using a series of pulsed lasers are disclosed herein.

In one example, a system for medical treatment includes a laser source, an optical module, and a controller coupled to the optical module. The laser source is configured to generate a series of pulsed lasers. The optical module is configured to provide a series of focused laser spots on a patient based on the series of pulsed lasers. The controller is configured to control the at least one of the optical module and a stage for holding the patient to move the series of focused laser spots on the patient to form a scan pattern.

In another example, a system for medical treatment includes a stage, a detection module, a laser source, an optical module, and a controller coupled to at least one of the optical module and the stage. The stage is configured to hold a patient. The detection module is configured to detect a treatment target of the patient. The laser source is configured to generate a series of pulsed lasers. The optical module is configured to provide a series of focused laser spots on the patient based on the series of pulsed lasers. The controller is configured to control the at least one of the optical module and the stage to move the series of focused laser spots on the patient to form a scan pattern based on the detected treatment target of the patient.

In a different example, a method for medical treatment is disclosed. A treatment target of a patient is detected. A series of pulsed lasers are generated. A series of focused laser spots are provided based on the series of pulsed lasers. The series of focused laser spots are moved on the patient to form a scan pattern based on the detected treatment target of the patient.

BRIEF DESCRIPTION OF THE DRAWINGS

The accompanying drawings, which are incorporated herein and form a part of the specification, illustrate embodiments of the present disclosure and, together with the description, further serve to explain the principles of the present disclosure and to enable a person skilled in the pertinent art to make and use the present disclosure.

Embodiments of the present disclosure will be described with reference to the accompanying drawings.

DETAILED DESCRIPTION

Although specific configurations and arrangements are discussed, this should be understood that this is done for illustrative purposes only. A person skilled in the pertinent art will recognize that other configurations and arrangements can be used without departing from the spirit and scope of the present disclosure. It will be apparent to a person skilled in the pertinent art that the present disclosure can also be employed in a variety of other applications.

It is noted that references in the specification to "one embodiment," "an embodiment," "an example embodiment," "some embodiments," etc., indicate that the embodiment described may include a particular feature, structure, or characteristic, but every embodiment may not necessarily include the particular feature, structure, or characteristic. Moreover, such phrases do not necessarily refer to the same embodiment. Further, when a particular feature, structure or characteristic is described in connection with an embodiment, it would be within the knowledge of a person skilled in the pertinent art to affect such feature, structure or characteristic in connection with other embodiments whether or not explicitly described.

In general, terminology may be understood at least in part from usage in context. For example, the term "one or more" as used herein, depending at least in part upon context, may be used to describe any feature, structure, or characteristic in a singular sense or may be used to describe combinations of features, structures or characteristics in a plural sense. Similarly, terms, such as "a," "an," or "the," again, may be understood to convey a singular usage or to convey a plural usage, depending at least in part upon context. In addition, the term "based on" may be understood as not necessarily intended to convey an exclusive set of factors and may, instead, allow for existence of additional factors not necessarily expressly described, again, depending at least in part on context.

In some existing systems for medical treatment using lasers, unfocused laser dots with relatively large size (e.g., larger than 1 mm diameter) are directly applied to blood vessels, teeth, bones, tumors, or other human tissues or organs. Although the single pulse energy is large in these systems, the energy density is relatively low due to the large size of laser dots. The high energy of the single pulsed laser can cause irrevocable damages to human tissues because of its peak power. On the other hand, the relatively long duration of the single pulsed laser (e.g., above 100 ps) can also cause thermal damages to human issues in proximity to the laser dots exposed area due to thermal conduction. In some other existing systems, a single pulsed laser can be split into multiple smaller laser dots distributed in an area, i.e., forming a dot matrix. However, as the laser energy is also divided into each laser dot, the energy density is also reduced.

Various embodiments in accordance with the present disclosure provide medical treatment systems using a series of focused laser spots based on low duration pulsed lasers. The laser energy density can be significantly increased by reduced laser spot size and duration of each pulsed laser, thereby greatly increasing treatment efficiency and effectiveness. Further, the reduced duration of each pulse laser (e.g., less than 50 ps) can avoid thermal damages to patients when it is shorter than the time needed for thermal conduction to surrounding human tissues. Moreover, by forming a series of focused laser spots over time, as opposed to an array of laser spots at the same time, the energy density of each laser spot is not sacrificed, and the treatment area and parameters can be easily controlled by adjusting the scan patterns formed by the series of focused laser spots.

Figure 1:
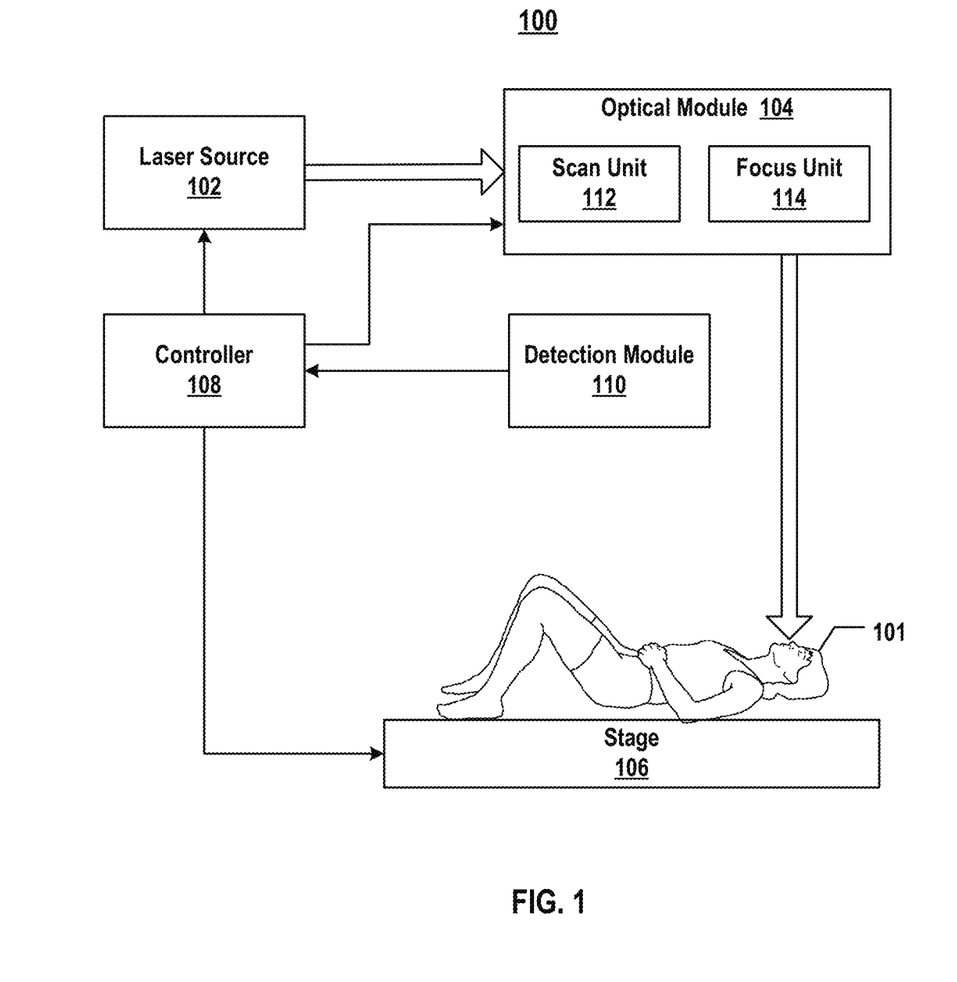
FIG. 1 illustrates a schematic diagram of an exemplary system for medical treatment using focused laser spots, according to some embodiments of the present disclosure.

FIG. 1 illustrates a schematic diagram of an exemplary system 100 for medical treatment using focused laser spots, according to some embodiments of the present disclosure. System 100 can include a laser source 102, an optical module 104, a stage 106, and a controller 108. Laser source 102 can be any suitable type of laser source including, but not limited to, fiber lasers, solid-state lasers, gas lasers, and semiconductor lasers. Laser source 102 can be configured to generate a series of pulsed lasers at any suitable wavelengths, such as 532 nm laser, 600-1,000 nm lasers, 1,064 nm laser, 1,550 nm laser, etc. In some embodiments, a duration of each pulsed laser is not greater than 50 picosecond (ps). The duration of each pulsed laser can be between 50 femtosecond (fs) and 50 ps, such as 50 fs, 60 fs, 70 fs, 80 fs, 90 fs, 100 fs, 200 fs, 300 fs, 400 fs, 500 fs, 600 fs, 700 fs, 800 fs, 900 fs, 1 ps, 2 ps, 3 ps, 4 ps, 5 ps, 6 ps, 7 ps, 8 ps, 9 ps, 10 ps, 20 ps, 30 ps, 40 ps, 50 ps, any range bounded by the lower end by any of these values, or in any range defined by any two of these values. In some embodiments, the duration of each pulsed laser is significantly below the scale of relaxation time needed for electron energy transferred to material lattice. As a result, each pulsed laser can stop before the thermal energy release by gasification can cause thermal effect to surrounding human tissues by thermal conduction.

Figure 3:
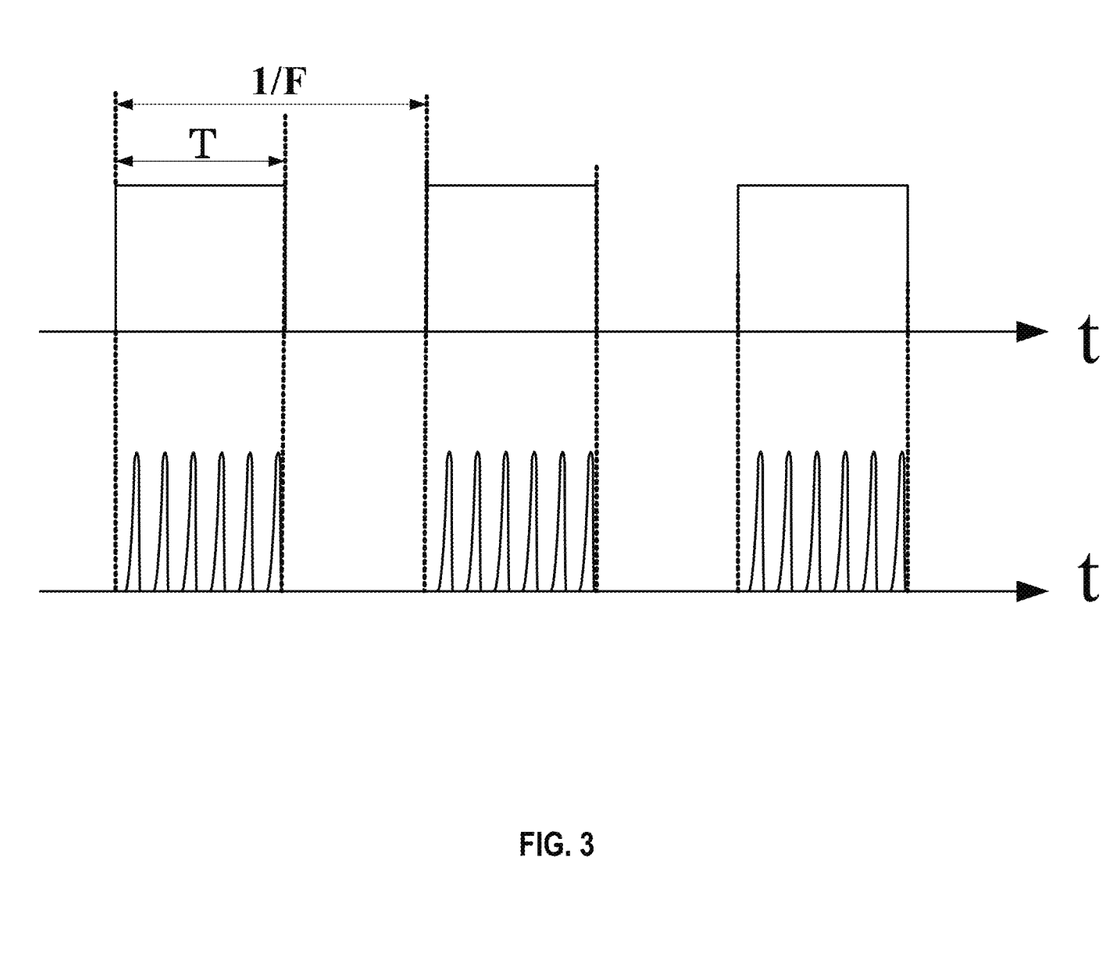
FIG. 3 illustrates exemplary pulsed lasers having a series of bursts, according to some embodiments of the present disclosure.

Each pulsed laser can be a single pulse or include a series of bursts. FIG. 3 illustrates exemplary pulsed lasers having a series of bursts, according to some embodiments of the present disclosure. The series of pulsed lasers can be generated by laser source at a frequency F, and the pulse width of each pulsed laser is T. When the pulsed lasers are generated in burst mode, N bursts can be generated in the same pulse width T, where N is an integer greater than 1, such as between 2 and 100. In some embodiments, the frequency of the bursts is in the scale of nanosecond (ns), and the frequency F of the laser pulses is in the scale of microsecond (μs). As a result, the laser energy can be first accumulated by the bursts within each pulse in the scale of ns and again accumulated by the pulses in the scale of μs, thereby achieving a very high energy density without the need of increasing the peak energy. That is, each focused laser spot may be formed by 1-N burst.

Referring back to FIG. 1, in some embodiments, the pulsed lasers generated by laser source 102 has a single wavelength, or a plurality of wavelengths, such as two or three different wavelengths. Pulsed lasers having different wavelengths can be separately, simultaneously, or alternatingly generated. In some embodiments, the wavelength of the pulsed lasers generated by laser source 102 is between 100 nm and 1,100 nm, such as 520 nm, 775 nm, or 1,040 nm. In some embodiments, the output frequency of laser source 102 is between 20 kHz and 1,000 kHz. In some embodiments, the average output power of laser source 102 is between 1 W and 100 W. It is understood that the parameters of pulsed lasers and laser source 102 disclosed above are for illustrative purposes only.

Optical module 104 can be optically coupled to laser source 102 and include a scan unit 112 and a focus unit 114. Optical module 104 can be configured to provide a series of focused laser spots on a patient 101 based on the series of pulsed lasers generated by laser source 102. In some embodiments, optical module is operatively coupled to controller 108 and receives control signals and instructions from controller 108. Scan unit 112 can be configured to, based on the control of controller 108, change directions in which at least some of the pulsed lasers emit to patient 101. That is, scan unit 112 can scan the pulsed lasers within a scan angle at a scan rate, as controlled by controller 108, toward patient 101. In some embodiments, scan unit 112 includes a galvanometer and/or a polarizer. Scan unit 112 can further include any other suitable scanning mirrors and scanning refractive optics.

Focus unit 114 can be configured to focus each of the pulsed lasers to form a series of focused laser spots. In some embodiments, a dimension of each of the focused laser spots is between 1 micrometer (μm) and 500 μm, such as 1 μm, 2 μm, 3 μm, 4 μm, 5 μm, 6 μm, 7 μm, 8 μm, 9 μm, 10 μm, 20 μm, 30 μm, 40 μm, 50 μm, 60 μm, 70 μm, 80 μm, 90 μm, 100 μm, 200 μm, 300 μm, 400 μm, 500 μm, any range bounded by the lower end by any of these values, or in any range defined by any two of these values. The shape of each focused laser spot can include, for example, round, rectangle, square, irregular, or any suitable shapes. In some embodiments, each focused laser spot has a substantially round shape with a diameter between 1 μm and 300 μm. It is understood that the dimensions of a series of focused laser spots can be substantially the same or different. By focusing the beams of pulsed lasers into focused laser spots, the energy density can be significantly increased.

Stage 106 can be configured to hold patient 101. In some embodiments, stage 106 includes an operating table, a hospital bed, or any suitable stage for holding patient 101 during the medical treatment. In some embodiments, stage 106 is further configured to, based on the control of controller 108, change positions of patient 101 during the medical treatment. Stage 106 can change the positions of the entire body or any parts of patient 101, such as the head, teeth, arms, legs, etc.

Controller 108 can be operatively coupled to laser source 102, optical module 104, and/or stage 106 and control the operations of laser source 102, optical module 104, and/or stage 106 via control signals and instructions. In some embodiments, controller 108 is configured to control optical module 104 and/or stage 106 to move the series of focused laser spots on patient 101 to form a scan pattern. As optical module 104 scans the focused pulsed lasers toward patient 101, any relative movement between stage 106 holding patient 101 and optical module 104 can cause movement of the focused laser spots on patient 101, thereby forming a scan pattern based on the relative movement. By controlling the relative movements between stage 106 and optical module 104, such as the direction and speed, controller 108 can control the scan pattern, e.g., the size and/or shape thereof, on patient 101. Moreover, controller 108 can further control the scan pattern by adjusting the parameters of the pulsed lasers generated by laser source 102 by controlling the operation of laser source 102. In some embodiments, the scan pattern is manually determined by a human operator, such as a doctor or medical technician, based on personal medical experience and knowledge, treatment rules, and/or observed conditions of patient 101. In some embodiments, the scan pattern is automatically or semi-automatically determined based on the treatment target (e.g., a tumor, tooth, lesion, etc.) of patient 101 by controller 108.

As shown in FIG. 1, in some embodiments, system 100 further includes a detection module 110 configured to prior to the medical treatment, detect the treatment target and provide detection data based on the treatment target to controller 108. Detection module 110 can include, but not limited to, a camera, a thermal imaging machine, an x-ray machine, an ultrasound machine, or any other suitable medical detection devices. It is understood that detection module 110 can be part of system 100 or a standalone device separate from system 100. For example, detection module 110 can be a dedicated medical imaging device that takes medical images of the treatment target of patient 101 and transmits the medical images, or any detection date derived from the medical images, to controller 108. It is further understood that the detection of the treatment target can be carried out based on any suitable modalities, such as images, videos, sounds, texts, etc. In addition to obtain initial detection data based on the initial detection of the treatment target of patient 101, in some embodiments, detection module 110 performs the detection continuously during the medical treatment or upon request by the human operator to monitor the status of the treatment, e.g., by detecting the scan pattern formed on patient 101.

In some embodiments, system 100 further includes a calibration unit (not shown) configured to calibrate positions of the focused laser spots on the patient. Controller 108 can be configured to control optical module 104 and/or stage 106 to move the series of focused laser spots on patient 101 based on the calibration performed by the calibration unit.

Figure 2:
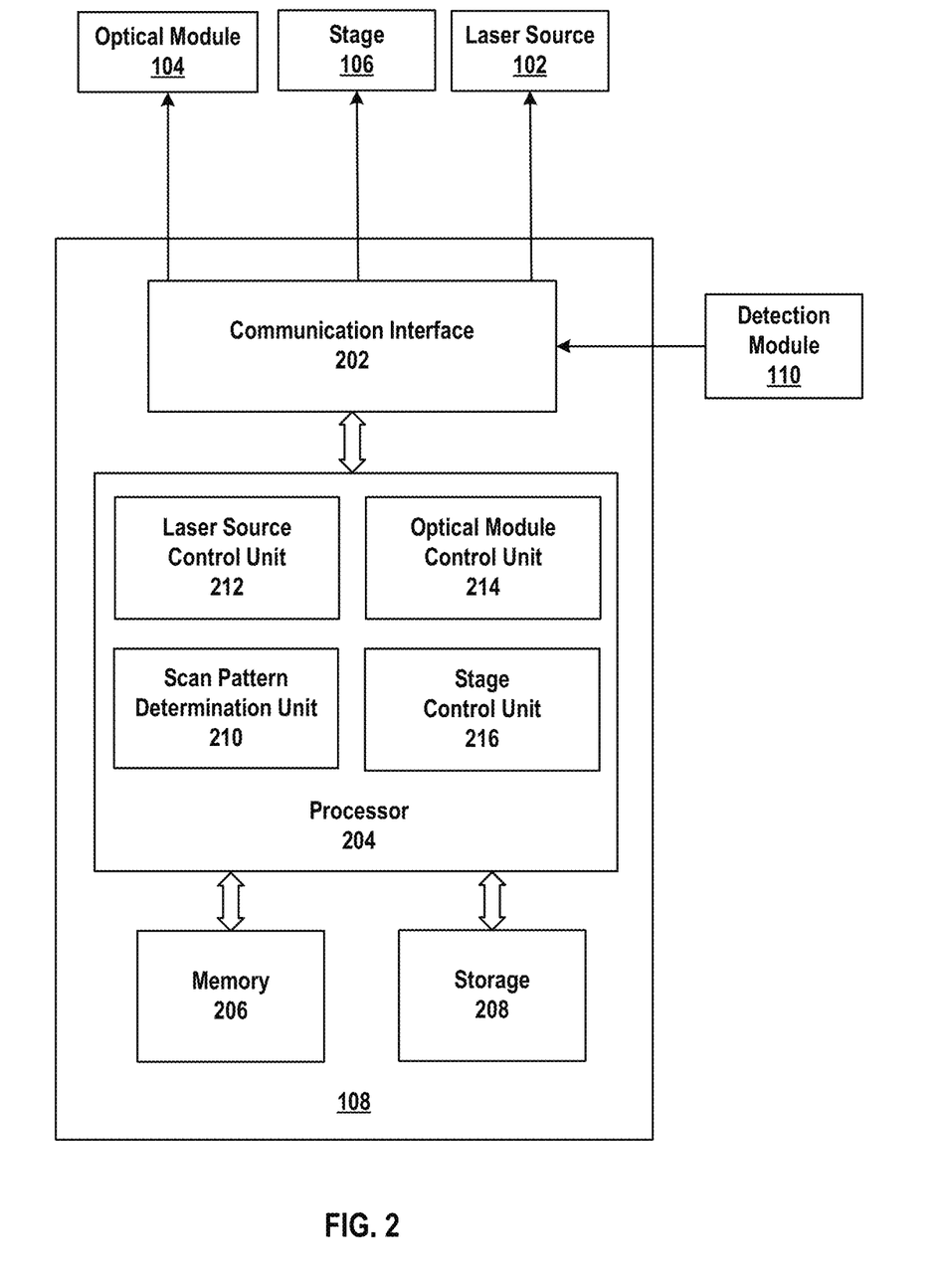
FIG. 2 illustrates a schematic diagram of an exemplary controller, according to some embodiments of the present disclosure.

FIG. 2 illustrates a schematic diagram of exemplary controller 108, according to some embodiments of the present disclosure. Controller 108 can control operations of laser source 102, optical module 104, and/or stage 106, for example, generate, adjust, and move a series of focused laser spots on patient 101 to form a scan pattern based on the detected treatment target of patient 101. In some embodiments, controller 108 receives detection data indicative of the treatment target of patient 101 and provides control instruction indicative of the scan pattern based on the detection data to laser source 102, optical module 104, and/or stage 106.

As shown in FIG. 2, controller 108 can include a communication interface 202, a processor 204, a memory 206, and a storage 208. In some embodiments, controller 108 has different modules in a single device, such as an integrated circuit (IC) chip (implemented as an application-specific integrated circuit (ASIC) or a field-programmable gate array (FPGA), or separate devices with dedicated functions. One or more components of controller 108 can be located along with laser source 102 and/or optical module 104 as part of system 100, or can be alternatively in a standalone computing device, in the cloud, or another remote location. Components of controller 108 can be in an integrated device or distributed at different locations but communicate with each other through a network (not shown). For example, processor 204 can be a processor on-board laser source 102 and/or optical module 104, a processor inside a standalone computing, or a cloud processor, or any combinations thereof.

Communication interface 202 may send data to and receive data from components such as laser source 102, optical module 104, stage 106, or detection module 110 via communication cables, a Wireless Local Area Network (WLAN), a Wide Area Network (WAN), wireless networks such as radio waves, a nationwide cellular network, and/or a local wireless network (e.g., Bluetooth™ or WiFi), or other communication methods. In some embodiments, communication interface 202 can be an integrated services digital network (ISDN) card, cable modem, satellite modem, or a modem to provide a data communication connection. As another example, communication interface 202 can be a local area network (LAN) card to provide a data communication connection to a compatible LAN. Wireless links can also be implemented by communication interface 202. In such an implementation, communication interface 202 can send and receive electrical, electromagnetic or optical signals that carry digital data streams representing various types of information via a network.

Processor 204 can include any appropriate type of general-purpose or special-purpose microprocessor, digital signal processor, or microcontroller. Processor 204 can be configured as a separate processor module dedicated to controlling laser source 102, optical module 104, and stage 106. Alternatively, processor 204 can be configured as a shared processor module for performing other functions unrelated to controlling laser source 102, optical module 104, and stage 106.

As shown in FIG. 2, processor 204 can include multiple modules, such as a scan pattern determination unit 210, a laser source control unit 212, an optical module control unit 214, a stage control unit 216, and the like. These modules (and any corresponding sub-modules or sub-units) can be hardware units (e.g., portions of an integrated circuit) of processor 204 designed for use with other components or to execute a part of a program. The program can be stored on a computer-readable medium, and when executed by processor 204, it may perform one or more functions. Although FIG. 2 shows units 210-216 all within one processor 204, it is contemplated that these units may be distributed among multiple processors located near or remotely with each other.

Scan pattern determination unit 210 can be configured to determine the scan pattern to be formed by the series of focused laser spots based on the treatment target of patient 101. In some embodiments, scan pattern determination unit 210 receives detection data indicative of a treatment target of patient 101 from detection module 110. As described above, depending on the type of medical treatment, the treatment target can be a lesion, tumor, tooth, part of the skin, blood vessel, or any other tissue or organ of patient 101. The detection data can be indicative of a texture, a shape, a color, and/or a defect of the treatment target, or any other suitable information associated with the treatment target that may be relevant to medical treatment thereof. For example, any suitable image processing algorithms can be implemented by scan pattern determination unit 210 to analyze the images of the treatment target and derive detection data from the analysis results in the forms of images, videos, sounds, texts, or metadata. In some embodiments, the image processing algorithms include pattern recognition algorithms that can automatically retrieve feature information of the treatment target, such as texture, shape, color, and defect, using machine learning based on training data.

In some embodiments, based on the detection data of the treatment target, scan pattern determination unit 210 generates the scan pattern for the treatment target to be formed by a series of focused laser spots. Specifically, scan pattern determination unit 210 can determine the size and/or shape of the scan pattern and the parameters of the series of focused laser spots that can form the scan pattern with the desired size and/or shape. For example, the parameters of the series of focused laser spots include, but not limited to, the path, speed, and/or repetition of the movement of the series of laser spots, size(s) of the laser spots, offset(s) of adjacent laser spots, density of the laser spots, repetitiveness of the laser spots, depth(s) of the laser spots under the skin, frequency of the laser spots, or any other parameters that can affect the size and/or shape of the scan pattern to be formed by the series of focused laser spots or the power applied by the focused laser spots on the patient during the medical treatment.

In addition to dynamically determining the initial scan pattern based on the treatment target of patient 101, in some embodiment, scan pattern determination unit 210 adaptively adjust the scan pattern in real time during the medical treatment. As described above, update of detection data can be continuously or upon request fed into scan pattern determination unit 210 during the medical treatment by detection module 110. The updated detection data can indicate the progress and status of the scan pattern as well as the treatment target during the medical treatment. Scan pattern determination unit 210 thus can adaptively adjust the parameters associated with the focused laser spots based on the current progress and status of the scan pattern and treatment target as reflected by the updated detection data. The subsequent focused laser spots can either follow the parameters associated with the initial scan pattern or be adjusted to follow the updated parameters. For example, the size and/or shape of the initial scan pattern can be adjusted to form an updated scan pattern. In another example, the path of movement of the subsequent focused laser spots can be adjusted to form an updated scan pattern.

Figure 4A:
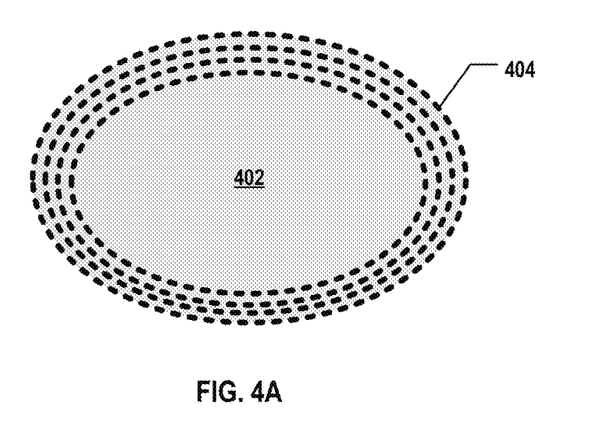
FIGS. 4A-4C illustrate various exemplary scan patterns formed by moving a series of focused laser spots based on treatment targets of a patient, according to various embodiments of the present disclosure.
Figure 4B:
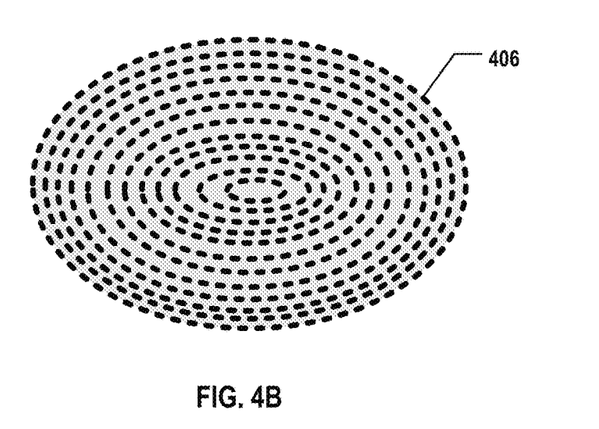
Figure 4C:
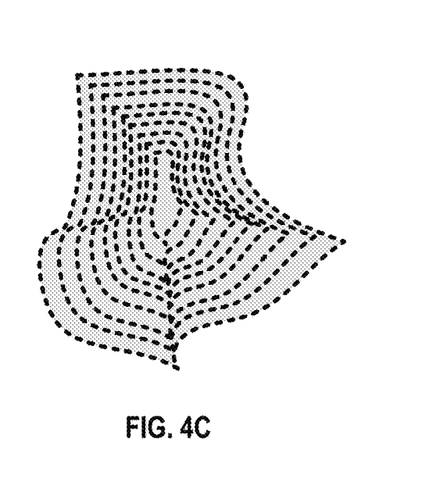

FIGS. 4A-4C illustrate various exemplary scan patterns formed by moving a series of focused laser spots based on treatment targets of a patient, according to various embodiments of the present disclosure. As shown in FIG. 4A, a treatment target 402 has an oval shape, and a scan pattern 404 is determined based on the shape and size of treatment target 402, for example, including a number of eclipses with gradually changing dimensions. Other parameters associated with the series of focused laser spots are determined as well, such as substantially rectangular shape, size, density, offset, etc. As shown in FIG. 4B, an updated scan pattern 406 is determined during the medical treatment based on the progress and status of initial scan pattern 404 and/or treatment target 402. It is understood that the shape of the treatment target is not limited to any regular shape, such as the oval shape shown in FIGS. 4A and 4B. For example, FIG. 4C shows a treatment target having an irregular shape, and a scan pattern can also be determined based on the irregular-shaped treatment target.

Figure 5:
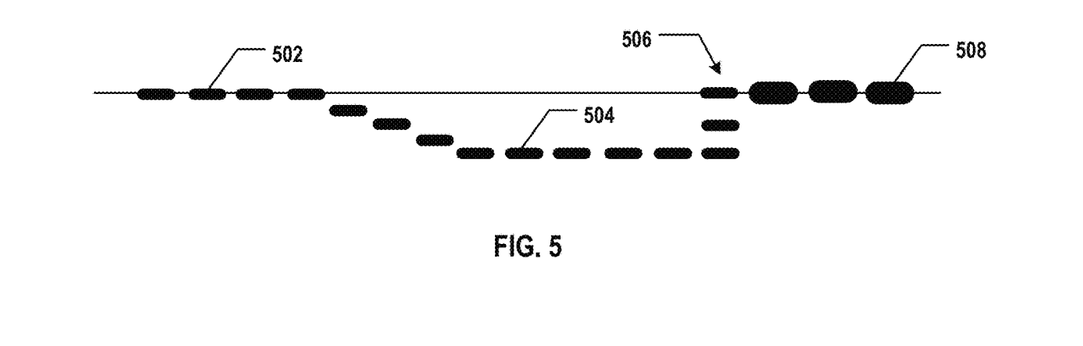
FIG. 5 illustrates a cross-section of an exemplary treatment target having a series of focused laser spots, according to some embodiments of the present disclosure.

FIG. 5 illustrates a cross-section of an exemplary treatment target having a series of focused laser spots, according to some embodiments of the present disclosure. FIG. 5 shows some parameters associated with the focused laser spots that can affect the scan pattern, such as depth and repetitiveness. As shown in FIG. 5, at region 502 of the scan pattern, a series of focused laser spots are on the surface of the skin without any repetition. The depth of the series of focused laser spots then starts to increase, e.g., going deeper into the skin, unit reaching to the deepest point at region 504. At region 506, a number of focused laser spots are repeatedly formed at the same location, but with different depths. At region 508, a number of focused laser spots are repeated formed at the same location with the same depth, e.g., forming larger laser spots. In some embodiments, the depth is between 0 and 500 µm under the skin. It is understood that the examples described above with respect to FIGS. 4A-4C and FIG. 5 are for illustrative purposes only, which show how scan pattern determination unit 210 can determine a scan pattern to be formed by a series of focused laser spots based on a treatment target of a patient.

It is understood that in forming the scan patterns, the series of focused laser spots may be substantially overlapped (e.g., greater than 50% of the number of focused laser spots forming the pattern are overlapped), partially overlapped (e.g., equal to less than 50% of the number of focused laser spots forming the pattern are overlapped), or not overlapped at all. The degree of overlapping between two or more adjacent focused laser spots may vary between 0 and 100% as well. In some embodiments, each of two adjacent focused laser spots are close to one another, but not overlapped, having a distance therebetween.

Referring back to FIG. 2, laser source control unit 212 can be configured to provide a control instruction to laser source 102 indicative of the initial scan pattern or the updated scan pattern. The control instruction can cause laser source 102 to initialize and adjust various parameters associated with the series of pulsed lasers based on the determined initial scan pattern or updated scan pattern prior to and during the medical treatment, respectively. In some embodiments, the power of laser source 102 is controlled by laser source control unit 212 to affect the size, shape, and or depth of the focused laser spots or the power applied by the focused laser spots on the patient. In some embodiments, the number of bursts in each of the pulsed lasers generated by laser source 102 is controlled by laser source control unit 212 to affect the size, shape, and or depth of the focused laser spots or the power applied by the focused laser spots on the patient. In some embodiments, the frequency of laser source 102 is controlled by laser source control unit 212 to affect the frequency and/or offset of the focused laser spots.

Optical module control unit 214 can be configured to provide a control instruction to optical module 104 indicative of the initial scan pattern or the updated scan pattern. The control instruction can cause optical module 104 to initialize and adjust various parameters associated with the series of pulsed lasers spots based on the determined initial scan pattern or updated scan pattern prior to and during the medical treatment, respectively. In some embodiments, scan unit 112 is controlled by optical module control unit 214 to affect the path, speed, and/or repetition of movement of the focused laser spots, which can in turn affect the power of the focused laser spots applied on the patient. In some embodiments, focus unit 114 is controlled by optical module control unit 214 to affect the size and/or shape of the focused laser spots, which can in turn affect the power of the focused laser spots applied on the patient.

Stage control unit 216 can be configured to provide a control instruction to stage 106 indicative of the initial scan pattern or the updated scan pattern. The control instruction can cause stage 106 to initialize and adjust various parameters associated with the movement of stage 106 based on the determined initial scan pattern or updated scan pattern prior to and during the medical treatment, respectively. In some embodiments, the direction and/or speed of movement of stage 106 is controlled by stage control unit 216 to affect the path, speed, and/or repetition of movement of the focused laser spots, which can in turn affect the power of the focused laser spots applied on the patient.

Memory 206 and storage 208 can include any appropriate type of mass storage provided to store any type of information that processor 204 may need to operate. Memory 206 and storage 208 can be a volatile or non-volatile, magnetic, semiconductor, tape, optical, removable, non-removable, or other type of storage device or tangible (i.e., non-transitory) computer-readable medium including, but not limited to, a ROM, a flash memory, a dynamic RAM, and a static RAM. Memory 206 and/or storage 208 can be configured to store one or more computer programs that may be executed by processor 204 to perform laser source 102, optical module 104, and stage 106 control functions disclosed herein. For example, memory 206 and/or storage 208 can be configured to store program(s) that may be executed by processor 204 to control operations of laser source 102, optical module 104, and stage 106, and process the data to generate control instructions and any other control signals.

Memory 206 and/or storage 208 can be further configured to store information and data used by processor 204. For instance, memory 206 and/or storage 208 can be configured to store the detection data indicative of the treatment target of patient 101 provided by detection module 110. The various types of data may be stored permanently, removed periodically, or disregarded immediately after each detection and/or scan.

Figure 6A:
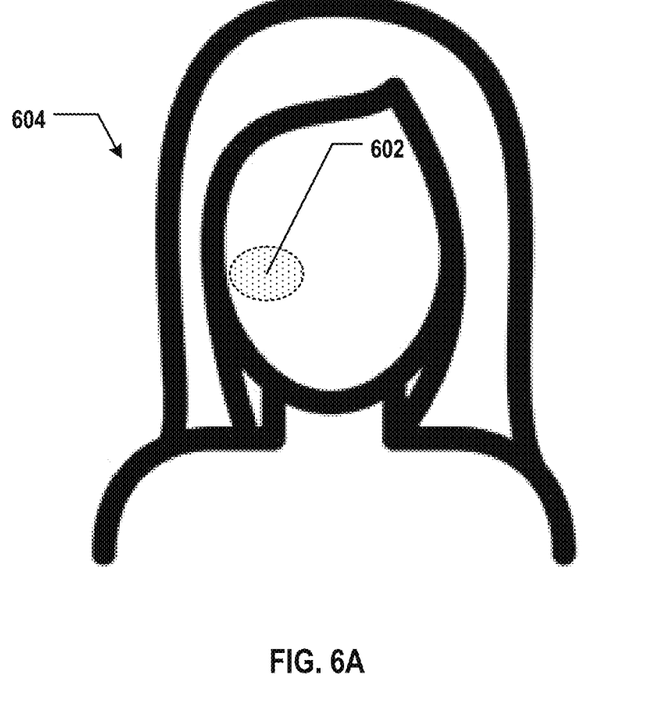
FIG. 6A illustrates an exemplary aesthetic medicine application of focused laser spots, according to some embodiments of the present disclosure.

FIG. 6A illustrates an exemplary aesthetic medicine application of focused laser spots, according to some embodiments of the present disclosure. As shown in FIG. 6A, a scan pattern 602 can be formed on a human face 604 or any other part of human bodies for aesthetic medicine applications on treatment targets, such as scars, pigmented lesion, tattoo, skin irregularities, signs of aging, skin laxity, wrinkles, moles, liver spots, excess fact, cellulite, unwanted hair, skin discoloration, and spider veins. Scan pattern 602 can be determined based on the treatment target on human face 604 and formed by the movement of a series of focused laser spots. The power, size, and/or shape of each of the focused laser spots can be precisely controlled for aesthetic medicine applications.

Figure 6B:
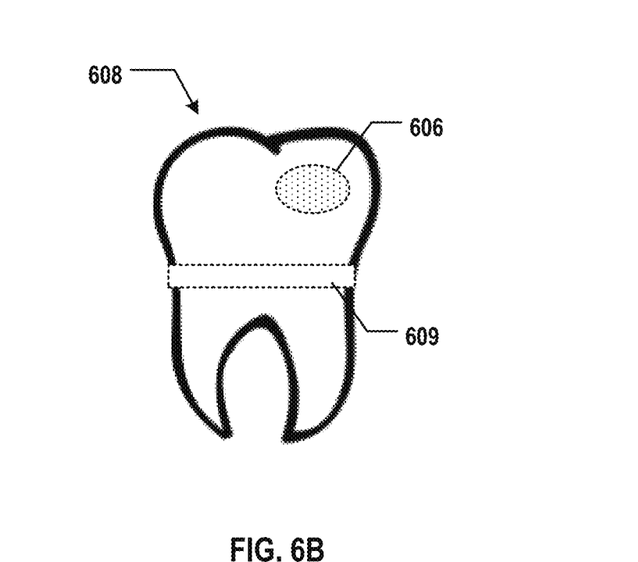
FIG. 6B illustrates an exemplary dental application of focused laser spots, according to some embodiments of the present disclosure.

FIG. 6B illustrates an exemplary dental application of focused laser spots, according to some embodiments of the present disclosure. As shown in FIG. 6B, a scan pattern 606 can be formed on a tooth 608 for teeth cleaning, such as removing dental plaque or decay. In some embodiments, a through hole 609 can be formed through tooth 608 by repeatedly applying a series of focused laser spots on a small region with very high energy density for dental surgery.

Figure 6C:
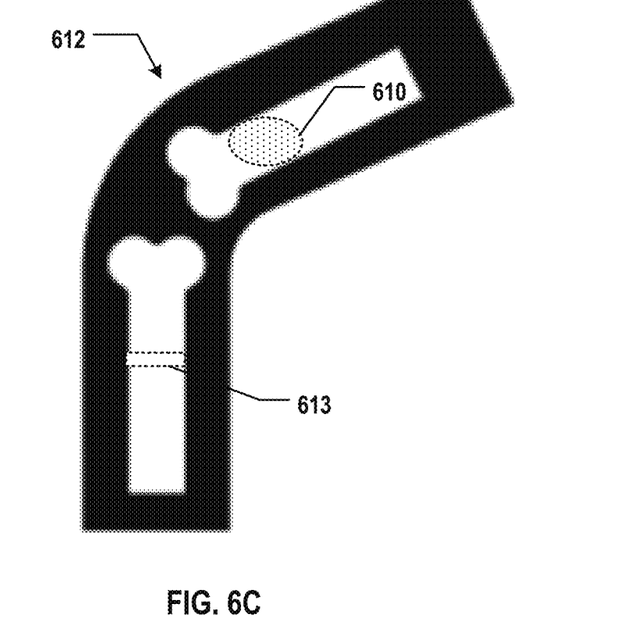
FIG. 6C illustrates an exemplary orthopedics application of focused laser spots, according to some embodiments of the present disclosure.

FIG. 6C illustrates an exemplary orthopedics application of focused laser spots, according to some embodiments of the present disclosure. As shown in FIG. 6C, a scan pattern 610 can be formed through the skin to the surface of a bone 612 to remove bone tissues. In some embodiments, a through hole 613 can be formed through bone 612 by repeatedly applying a series of focused laser spots on a small region with very high energy density for bone surgery.

Figure 6D:
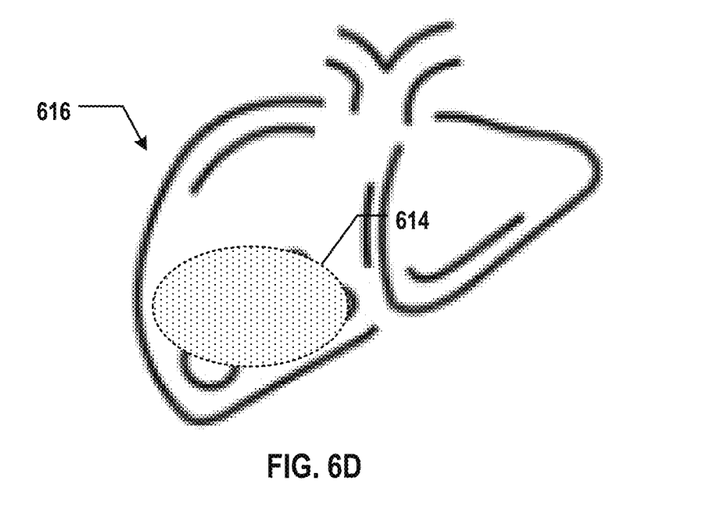
FIG. 6D illustrates an exemplary oncology application of focused laser spots, according to some embodiments of the present disclosure.

FIG. 6D illustrates an exemplary oncology application of focused laser spots, according to some embodiments of the present disclosure. As shown in FIG. 6D, a scan pattern 614 can be formed through the skin to the surface of an organ 616 to precisely remove tumor formed on organ 616. Scan pattern 614 can be determined based on the tumor and formed by the movement of a series of focused laser spots.

Figure 7:
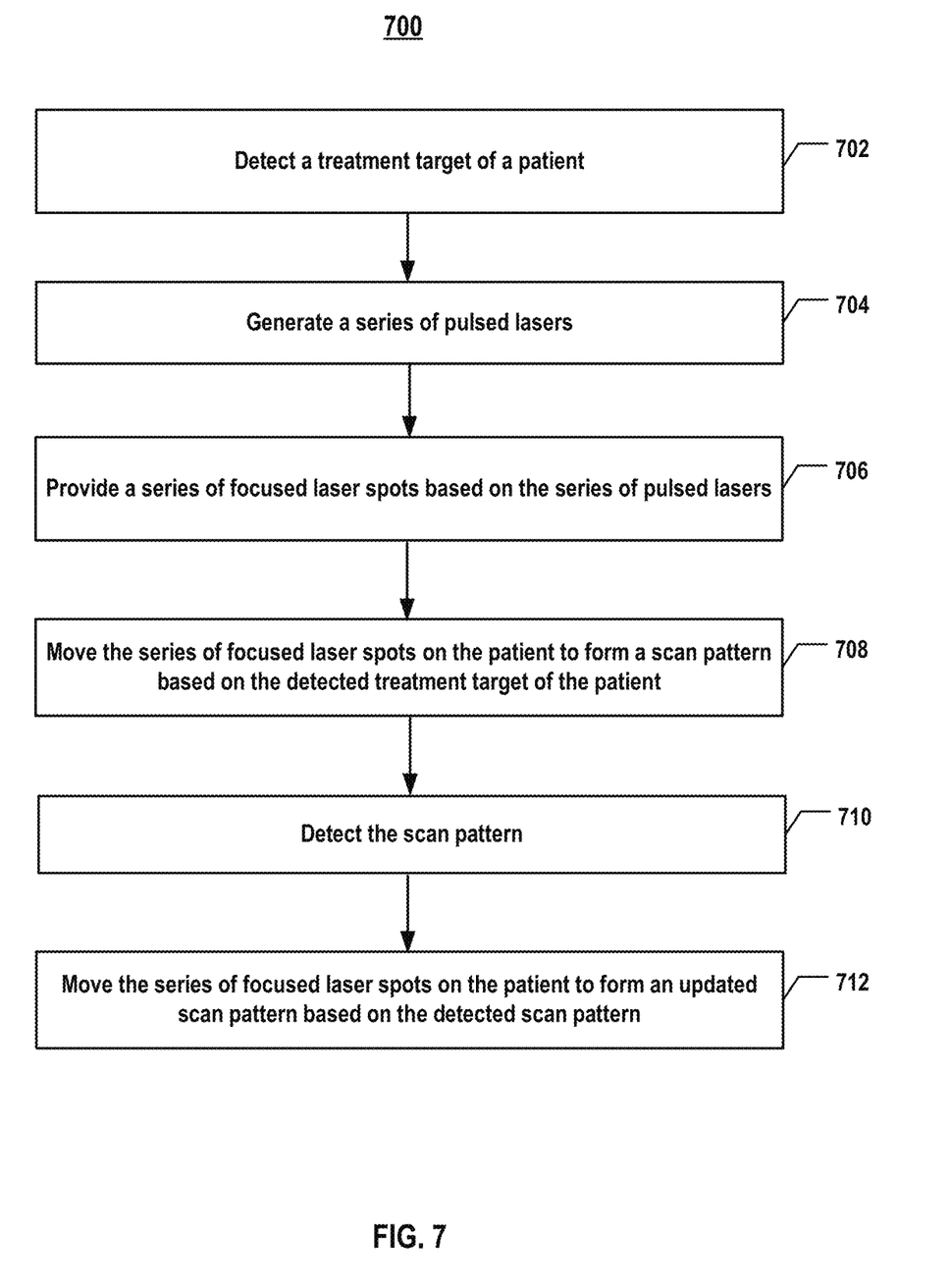
FIG. 7 is a flowchart of a method for medical treatment using focused laser spots, according to some embodiments.

FIG. 7 is a flowchart of a method 700 for medical treatment using focused laser spots, according to some embodiments. It is understood that the operations shown in method 700 are not exhaustive and that other operations can be performed as well before, after, or between any of the illustrated operations. Further, some of the operations may be performed simultaneously, or in a different order than shown in FIG. 7.

Referring to FIG. 7, method 700 starts at operation 702, in which a treatment target of a patient is detected. In some embodiments, detection data indicative of the treatment target of the patient is obtained. Operation 702 is implemented by detection module 110 of system 100 prior to the medical treatment of patient 101. In some embodiments, the detection of the treatment target is manually performed by a human operator.

Method 700 proceeds to operation 704, as illustrated in FIG. 7, in which a series of pulsed lasers are generated. In some embodiments, the duration of each of the pulsed lasers is not greater than 50 ps, for example, between 50 fs and 50 ps. In some embodiments, each of the pulsed lasers includes a series of bursts. Operation 704 can be implemented by laser source 102 of system 100.

Method 700 proceeds to operation 706, as illustrated in FIG. 7, in which a series of focused laser spots are provided based on the series of pulsed lasers. In some embodiments, to provide the series of focused laser spots, each of the pulsed lasers is focused, such that a dimension of each of the focused laser spots is between 1 μm and 500 μm. Operation 706 can be implemented by optical module 104 of system 100.

Method 700 proceeds to operation 708, as illustrated in FIG. 7, in which the series of focused laser spots are moved on the patient to form a scan pattern based on the detected treatment target of the patient. In some embodiments, to move the series of focused laser spots, directions in which at least some of the pulsed laser emit to the patient are changed, for example, by scan unit 112 of optical module 104. In some embodiments, to move the series of focused laser spots, positions of the patient are changed during the medical treatment, for example, by stage 106 of system 100. In some embodiments, a control instruction indicative of the scan pattern is provided, for example, by controller 108 of system 100, based on the detection data obtained by, for example, detection module 110. In some embodiments, positions of the focused laser spots on the patient are first calibrated, such that the movement of the series of focused laser spots on the patient is based on the calibration. In some embodiments, at least some of the focused laser spots are formed at different depths under a skin of the patient.

Method 700 proceeds to operation 710, as illustrated in FIG. 7, in which the scan pattern is detected during the medical treatment. Operation 710 is implemented by detection module 110 during the medical treatment of patient 101. In some embodiments, the detection of the scan pattern is manually performed by a human operator.

Method 700 proceeds to operation 712, as illustrated in FIG. 7, in which the series of focused laser spots are moved on the patient to form an updated scan pattern based on the detected scan pattern. In some embodiments, updated detection data is provided, for example, by detection module 110 to controller 108, based on the detection of the scan pattern. In some embodiments, the size and/or shape of the scan pattern are adjusted to form the updated scan pattern. In some embodiments, a path of the movement of the focused laser spots on the patient is adjusted to form the updated scan pattern. In some embodiments, powers applied by the focused laser spots on the patient are adjusted during the medical treatment. In one example, the powers are adjusted by adjusting the power of the laser source and/or the number of bursts in each of the pulsed lasers. In another example, the powers are adjusted by adjusting the speed and/or repetition of the movement of the focused laser spots.

Another aspect of the disclosure is directed to a non-transitory computer-readable medium storing instructions which, when executed, cause one or more processors to perform the methods, as discussed above. The computer-readable medium may include volatile or non-volatile, magnetic, semiconductor, tape, optical, removable, non-removable, or other types of computer-readable medium or computer-readable storage devices. For example, the computer-readable medium may be the storage device or the memory module having the computer instructions stored thereon, as disclosed. In some embodiments, the computer-readable medium may be a disc or a flash drive having the computer instructions stored thereon.

The foregoing description of the specific embodiments will so reveal the general nature of the present disclosure that others can, by applying knowledge within the skill of the art, readily modify and/or adapt for various applications such specific embodiments, without undue experimentation, without departing from the general concept of the present disclosure. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

Embodiments of the present disclosure have been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The Summary and Abstract sections may set forth one or more but not all exemplary embodiments of the present disclosure as contemplated by the inventor(s), and thus, are not intended to limit the present disclosure and the appended claims in any way.

The breadth and scope of the present disclosure should not be limited by any of the above-described exemplary embodiments, but should be defined only in accordance with the following claims and their equivalents.

What is claimed is:

1. A system for medical treatment, comprising:
a detection module configured to detect a treatment target of a patient and generate detection data indicative of the treatment target prior to the medical treatment;
a laser source configured to generate a series of pulsed lasers;
an optical module configured to provide a series of focused laser spots on the patient based on the series of pulsed lasers; and
a controller coupled to the optical module and configured to control at least one of the optical module and a stage for holding the patient to move the series of focused laser spots on the patient to form a scan pattern based on the detection data received from the detection module,
wherein the detection module is further configured to detect the scan pattern during the medical treatment and provide updated detection data to the controller based on the detection of the scan pattern; and
the controller is further configured to control the at least one of the optical module and the stage to move the series of focused laser spots on the patient to form an updated scan pattern based on the updated detection data.

2. The system of claim 1, wherein a duration of each of the pulsed lasers is not greater than 50 picosecond (ps).

3. The system of claim 2, wherein the duration of each of the pulsed lasers is between 50 femtosecond (fs) and 50 ps.

4. The system of claim 1, wherein each of the pulsed lasers includes a series of bursts, and each of the focused laser spots is formed by the series of bursts.

5. The system of claim 1, wherein the optical module comprises a focus unit configured to focus each of the pulsed lasers so that a dimension of each of the focused laser spots is between 1 micrometer (μm) and 500 μm.

6. The system of claim 1, wherein the optical module comprises a scan unit configured to, based on the control of the controller, change directions in which at least some of the pulsed lasers emit to the patient.

7. The system of claim 1, wherein the stage is configured to, based on the control of the controller, change positions of the patient during the medical treatment.

8. The system of claim 1, wherein the detection data is indicative of at least one of a texture, a shape, a color, and a defect of the treatment target.

9. The system of claim 1, wherein the controller is further configured to adjust a size and/or a shape of the scan pattern to form the updated scan pattern.

10. The system of claim 1, wherein the controller is further configured to adjust a path of the movement of the focused laser spots on the patient to form the updated scan pattern.

11. The system of claim 1, further comprising a calibration unit configured to calibrate positions of the focused laser spots on the patient,
wherein the controller is configured to control the at least one of the optical module and the stage to move the series of focused laser spots on the patient based on the calibration.

12. The system of claim 1, wherein the controller is further configured to adjust powers applied by the focused laser spots on the patient during the medical treatment.

13. The system of claim 12, wherein, to adjust the powers applied by the focused laser spots on the patient, the controller is further coupled to the laser source and configured to control the laser source to adjust at least one of a power of the laser source and a number of bursts in each of the pulsed lasers.

14. The system of claim 12, wherein, to adjust the powers applied by the focused laser spots on the patient, the controller is further configured to control the at least one of the optical module and the stage to adjust at least one of a speed and a repetition of the movement of the focused laser spots.

15. The system of claim 1, wherein at least some of the focused laser spots are formed at different depths under a skin of the patient.

16. The system of claim 1, wherein at least some of the focused laser spots are overlapped.

17. A system for medical treatment, comprising:
a stage configured to hold a patient;
a detection module configured to detect a treatment target of the patient and generate detection data indicative of the treatment target prior to the medical treatment;
a laser source configured to generate a series of pulsed lasers;
an optical module configured to provide a series of focused laser spots on the patient based on the series of pulsed lasers; and
a controller coupled to at least one of the optical module and the stage and configured to control at least one of the optical module and the stage to move the series of focused laser spots on the patient to form a scan pattern based on the detection data received from the detection module,
wherein the detection module is further configured to detect the scan pattern during the medical treatment and provide updated detection data to the controller based on the detection of the scan pattern; and
the controller is further configured to adjust at least one of (i) a size of the scan pattern, (ii) a shape of the scan pattern, or (iii) a path of the movement of the focused laser spots on the patient to form an updated scan pattern.

18. A method for medical treatment, comprising:
detecting a treatment target of a patient prior to the medical treatment;
generating detection data indicative of the treatment target;
generating a series of pulsed lasers;
providing a series of focused laser spots based on the series of pulsed lasers; moving the series of focused laser spots on the patient to form a scan pattern based on the detection data;
detecting the scan pattern during the medical treatment;
providing updated detection data based on the detection of the scan pattern; and
moving the series of focused laser spots on the patient to form an updated scan pattern based on the updated detection data.

19. The method of claim 18, wherein a duration of each of the pulsed lasers is not greater than 50 ps.

20. The method of claim 19, wherein the duration of each of the pulsed lasers is between 50 fs and 50 ps.

21. The method of claim 18, wherein each of the pulsed lasers includes a series of bursts, and each of the focused laser spots is formed by the series of bursts.

22. The method of claim 18, wherein providing the series of focused laser spots comprises focusing each of the pulsed lasers so that a dimension of each of the focused laser spots is between 1 μm and 500 μm.

23. The method of claim 18, wherein moving the series of focused laser spots comprises changing directions in which at least some of the pulsed lasers emit to the patient.

24. The method of claim 18, wherein moving the series of focused laser spots comprises changing positions of the patient during the medical treatment.

25. The method of claim 18, further comprising adjusting a size and/or a shape of the scan pattern to form the updated scan pattern.

26. The method of claim 18, further comprising adjusting a path of the movement of the focused laser spots on the patient to form the updated scan pattern.

27. The method of claim 18, further comprising
calibrating positions of the focused laser spots on the patient; and
moving the series of focused laser spots on the patient based on the calibration.

28. The method of claim 18, further comprising adjusting powers applied by the focused laser spots on the patient during the medical treatment.

29. The method of claim 28, wherein adjusting the powers applied by the focused laser spots on the patient comprises adjusting at least one of a power of the laser source and a number of bursts in each of the pulsed lasers.

30. The method of claim 28, wherein adjusting the powers applied by the focused laser spots on the patient comprises adjusting at least one of a speed and a repetition of the movement of the focused laser spots.

* * * * *